United States Patent [19]
Rutner et al.

[11] Patent Number: 5,366,895
[45] Date of Patent: Nov. 22, 1994

[54] METHOD FOR LYSING LIPOSOMES USING POLYETHYLENEGLYCOL MONONONYLPHENYL ETHERS

[75] Inventors: Herman Rutner, Hackensack, N.J.; Abdul M. Butt, New City, N.Y.; Josephine D. Readio, Sparta, N.J.; Lewis Pollack, Riverdale, N.Y.

[73] Assignee: Becton, Dickinson and Company, Franklin Lakes, N.J.

[21] Appl. No.: 489,304

[22] Filed: Mar. 5, 1990

[51] Int. Cl.$^5$ .................. G01N 33/543; G01N 33/546
[52] U.S. Cl. ........................ 436/17; 436/533; 436/800; 436/829; 436/71; 436/172; 436/8
[58] Field of Search ............ 435/4, 7, 8, 14, 25, 435/28, 7.1; 436/520, 522, 546, 829, 537, 172, 71, 17, 518, 8, 533, 800

[56] References Cited

U.S. PATENT DOCUMENTS 4,707,441 11/1987 Ahmad et al. .................. 435/7
4,713,324 12/1987 Fox et al. ........................ 435/4
4,743,560 5/1988 Campbell et al. ............. 436/501

OTHER PUBLICATIONS

Makarova, T. V. et al. "The investigation of high-temperature transition in egg yolk lecithin liposomes", Biol. Nauki (Moscow), (5), 23–31, 1988, (English translation).

M. Sila et al., "Effects of Triton X-100 Concentration and Incubation Temperature On Carboxyfluorescein Release From Multimellar Liposomes," Biochimica et Biophysica Acta 859 (1986), pp. 165-170.

Ethonic TM Alcohol Ethoxylates, Technical Bulletin and Product Bulletin.

Primary Examiner—James C. Housel
Assistant Examiner—David Redding
Attorney, Agent, or Firm—Royal N. Ronning, Jr.; Susan A. Capello

[57] ABSTRACT

A method for rapidly lysing liposomes having transition temperatures in the range of 35° to 65° C. is provided. Such liposomes are treated with a surfactant including

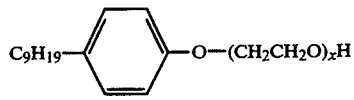

wherein x represents an average of 9 or 12. The method is applicable to fluorescence immunoassay procedures.

11 Claims, No Drawings

METHOD FOR LYSING LIPOSOMES USING POLYETHYLENEGLYCOL MONONONYLPHENYL ETHERS

BACKGROUND OF THE INVENTION

The invention relates to the use of surfactants for lysing liposomes, particularly for the liposomes that have high transition temperatures between 35° and 65° C.

Liposomes are frequently used as drug delivery vehicles which allow entrapped molecules to escape under various conditions and after various periods of time. In an article by M. Sila et al. entitled "Effects of Triton X-L100 Concentration and Incubation Temperature on Carboxyfluorescein Release from Multilamellar Liposomes", as published in *Biochimica et Biophysica Acta* 859 (1986), pp. 165-170, the lysis of various multilamellar liposomes with Triton-X is described. Carboxyfluorescein is a fluorescent dye which is commonly used as a marker to determine the razes at which water-soluble substances leak from liposomes. The three "hard" liposomes discussed in the article contained saturated phospholipids. Specifically, distearoyl-L-α-phosphatidylcholine/cholesterol (2:1 mole ratio,), dipalmitoyl-L-α-phosphatidylcholine and L-aphosphatidylcholine were tested. The carboxyfluorescein was excited by a spectrofluorometer at 490 nm and the emitted light read at 520 nm. The experiments showed that the use of Rohm and Haas' Triton X-100(polyethyleneglycol (9-10) p-toctylphenol) as a lysing agent did not result in the instantaneous destabilization of the liposome and release of the marker. The amount and rate of release were found to be dependent on the lipid composition of the liposome, the concentration of the Triton X-100, and the temperature and duration of incubation.

In contrast, U.S. Pat. No. 4,707,441 is directed to the use of liposome-compatible surfactants in connection with "soft" liposomes, i.e. those made from egg lecithin, containing unsaturated phospholipids. A number of surfactants, including those sold under the trade names Igepal (GAF Corp.) and Triton (Rohm and Haas), were tested. Some of them were found to lyse liposomes and were therefore unsuitable for the purposes described in the patent.

U.S. Pat. No. 4,713,324 discloses the lysis of liposomes by detergents or by immunological reaction. The liposome may contain one of a variety of markers such as tempocholine, a fluor and a quencher, or potassium ions. In one test, the serum levels of theophylline, a drug used to treat bronchial asthma, was determined. The "soft" liposomes for this test were formed from egg lecithin. The marker used was a chemiluminescent compound in tris (hydroxymethyl) aminomethane buffer. Triton X-100 was used to lyse the liposomes. The luminescence of intact and lysed liposomes were measured and analyzed.

While Triton X-100 was found to be effective for lysing some liposomes, particularly those having relatively low transition temperatures, it is only marginally effective upon more difficult-to-lyse liposomes, particularly those containing phospholipids with relatively high transition temperatures (e.g. stearoyl phosphatides). Sodium deoxycholate and sodium dodecylsulfate (SDS) are two other compounds frequently employed to effect lysis.

SUMMARY OF THE INVENTION

It is an object of the invention to provide a method for rapidly lysing difficult-to-lyse liposomes.

It is another object of the invention to provide a method for treating liposomes containing a marker such that signal stability is achieved within a very short period of time after initiation of lysis.

Signal reproducibility, signal enhancement and low toxicity are three additional objects of the method according to the invention.

In accordance with these and other objects of the invention, a method for lysing liposomes is provided with comprises treating the liposomes to be lysed with a surfactant selected from

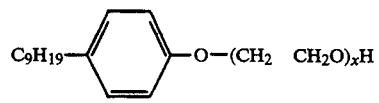

wherein x represents an average of 9 or 12. The liposomes to be lysed have transition temperatures in the range of 35° to 65° C.

The polyethyleneglycol mononunylphenyl ethers used in accordance with the invention provide superior lysing of liposomes having the above-referenced transition temperatures. Markers within the liposomes are accordingly rapidly released. Detecting equipment, which is used to detect the presence of the releasing marker, is able to generate a stable response shortly after lysing.

DETAILED DESCRIPTION OF THE INVENTION

The present invention provides a method for lysing liposomes through the use of polyethyleneglycol mononunylphenyl ethers. The lysing may be for the purpose of releasing markers or other substances entrapped within the liposomes.

Certain types of liposomes having transition temperatures below about 35° C. are relatively easy to lyse. Conventional lysing agents are accordingly satisfactory for treating such liposomes as lysis will occur quite rapidly. Sufficiently rapid lysing may not occur when "hard" liposomes are employed, i.e. liposomes having transition temperatures between about 35° to 65° C. Such liposomes are preferred for encapsulating various substances, including markers, used in commercial diagnostic systems which are frequently exposed to stressful conditions such as high temperatures during storage or transport. However, if the markers, such as fluorescent dyes, are not rapidly released upon addition of the lysing agent, it not only takes an undue amount of time for a stable signal from the detecting equipment to be generated, but also impairs signal reproducibility from test to test.

It has been found that surfactants having the following formula provide rapid lysing of even difficult-to-lyse liposomes:

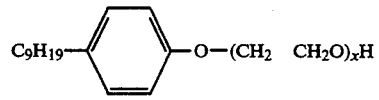

wherein x represents an average of 9 or 12. These compounds are commercially available, e.g. from GAF Corporation under the trademarks Igepal CO-630 (x=9) and Igepal CO-720 (x=12).

Five criteria have been established for determining the effectiveness of lysing agents used in connection width marker-containing liposomes: 1) lysing rate; 2) signal stability; 3) signal reproducibility; 4) signal enhancement; and 5) low toxicity. The first four criteria are measured by treating a liposome containing a dye (e.g. a fluorescent dye) with the surfactant being studied and measuring the extent of lysis either by absorbance or by fluorescence. A spectrophotometer is used to detect the absorbance characteristics of the dye prior and subsequent to lysis. Two types of signals are generated by the equipment, a quenched signal and an unquenched signal. The quenched signal is generated when the dye is in its concentrated state within the liposomes. An unquenched signal is generated when the dye is diluted in a bulk solution, where it would exist after the liposome is lysed by the surfactant. In fluorometry, the quenched signal is essentially zero and only the unquenched is measured.

The most important characteristic of a lysing agent as described above is the lysing rate. This rate is measured by the time it takes to lyse essentially all of the liposomes. Ideally, complete lysing occurs instantaneously.

Signal stability is measured by determining the coefficient of variation (CV) of the signal over a period of time, starting with the signal immediately after lysis. Signal reproducibility is determined by comparing the signals generated by the detecting equipment during separate tests of the same lysed solution. Signal enhancement refers to the inhibition by the surfactant of signal quenching, and is an empirical observation. Water tends to quench fluorescence. Micelles or aggregations of the lysing agent may tend to trap some of the fluorescent material, thereby shielding it from the water which would otherwise tend to quench fluorescence.

One of the procedures in which the phenyl ethers according to the invention may be utilized is in determining theophylline (1, 3-dimethylxanthine) concentrations in blood serum. Theophylline, when prescribed for the treatment of asthma and other bronchial conditions, is maintained between 10-20 $\mu$g/ml. Since absorption and clearance of the drug differ from patient to patient, testing is required to monitor its concentration levels.

One test makes use of liposomes ($C_{18}$:0 distearoyl phosphatides) which contain a fluorescent dye (sulforhodamine B) and incorporate immunological properties. The dye is almost completely self-quenched within the liposomes. The immunological properties are the result of theophylline which is attached to the surfaces of the liposomes. The liposomes act as labeling agents and compete with theophylline in the patient serum for the limited numbers of binding sites on theophylline antibodies which are coated on a plastic tube. After incubation, the unbound liposomes are separated from the antibody-bound fraction by decanting and rinsing the tube. A dilute detergent is then added to the tube to lyse the liposomes and release the dye. Since the starting concentration of liposomes is constant, the resulting fluorescence is inversely proportional to the concentration of theophylline in the patient sample. This test is known as fluorescence immunoassay (FIA).

In accordance with this test, three test tubes are provided. The first tube contains theophylline liposomes within a buffer solution of deionized water, and a preservative such as 0.02% sodium azide. The liquid volume is about 1.0 ml. The second tube contains theophylline monoclonal antiserum coated upon the tube. The buffer maintains the pH at about 7.4 during subsequent mixing of the contents of the tubes. The third tube contains a dilute detergent solution in deionized water, with preservative. A liquid volume of about 2.0 ml is provided in the third tube.

A volume of about 0.05 to 0.20 ml of serum is added to the first tube which contains the liposomes. The serum-liposome mixture is transferred to the second tube by coupling the first and second tubes at their open ends and inverting them several times. After incubating the coupled tubes at 25°-45° C. for about ten minutes, the tubes are uncoupled and the first tube discarded with any liquid therein. All residual incubate is also removed from the second tube by rinsing it with a saline solution and tapping the bottom of the tube.

Since the test results may be affected by the length of time between washing and commencement of lysing, the detergent in the third tube should be added to the second tube as soon as possible. The second and third tubes are coupled at their open ends, inverted several times, and placed in a fluorometer for analysis.

While the above test has been conducted using a lysing agent consisting of about 1% Triton X-100, 10% tetrahydrofurfuryl alcohol, and the remainder deionized water, the toxicity and bad odor of this agent makes it undesirable.

The liposomes employed for the test procedure preferably have a relatively high transition temperature to provide superior stability under stress conditions. This characteristic also allows them to be stored without risk of damage or deterioration unless temperatures exceed at least about 55° C. The drawback, which is overcome by the present invention, is that such liposomes are more difficult to lyse. The liposome is essentially a fatty cell including a lipid bilayer which contains water and a concentrated dye. The dye is essentially self-quenched until lysis occurs. As discussed above, lysis must occur rapidly upon introduction of the lysing agent in order for the fluorometer to provide accurate and repeatable measurements.

EXAMPLE I

Table I, shown below, demonstrates the excellent signal stability and enhancement provided by the compounds employed in accordance with the invention. The tests were conducted at room temperature using 1% solutions of the listed lysing agents except for agent no. 2, which also included 10% tetrahydrofurfuryl alcohol (THFA). A suspension of digoxin liposomes containing sulforhodamine B dye was added to the lysing agents. The extent of lysing was monitored fluorometrically by measuring the absorbances (A) at 531 and 565 nm at fixed intervals over a period of four (4) minutes.

TABLE 1

LYSIS OF UNBOUND DIGOXIN LIPOSOMES

| Lysing Agent | $A_{565}1$ | % C.V. | $A_{531}1$ | % C.V. | $Ratio_2$ |
|---|---|---|---|---|---|
| 1. Triton X-100 | 0.3634 | 0.15 | 0.1371 | 0.62 | 0.99 |
| 2. Triton/THFA | 0.3658 | 0.12 | 0.1429 | 0.37 | 1.00 |
| 3. CO-630 | 0.3709 | 0.09 | 0.1418 | 0.25 | 1.01 |
| 4. CO-720 | 0.3561 | 0.07 | 0.1492 | 0.26 | 0.97 |
| 5. C-850[3] | 0.3255 | 0.05 | 0.1728 | 0.21 | 0.89 |
| 6. CO-890[4] | 0.2665 | 0.12 | 0.2121 | 0.27 | 0.73 |
| 7. CO-990[5] | 0.2412 | 0.14 | 0.2293 | 0.14 | 0 66 |

TABLE 1-continued

| LYSIS OF UNBOUND DIGOXIN LIPOSOMES | | | | | |
|---|---|---|---|---|---|
| Lysing Agent | $A_{565}1$ | % C.V. | $A_{531}1$ | % C.V. | $Ratio_2$ |
| 8. Tween-20[6] | 0.2784 | 0.21 | 0.2171 | 0.27 | 0.76 |
| 9. Tween-40[7] | 0.2358 | 0.87 | 0.2517 | 0.78 | 0.65 |
| 10. Tween-80[8] | 0.2544 | 0.16 | 0.2349 | 0.19 | 0.70 |
| 11. Na deoxycholate | 0.2538 | 0.43 | 0.2167 | 0.35 | 0.69 |
| 12. Na dodecylsulfate | 0.2361 | 0.32 | 0.2418 | 0.16 | 0.65 |

1. Absorbance: Mean value and % CV of 10 RFU measurements taken between 0.5 and 4 minutes after addition of lysing agent.
2. Signal ratio relative to lysis agent #2, Triton X-100 in 10% tetrahydrofurfuryl alcohol (THFA), measured at 565 nm
3,4,5. These surfactants are homologs of agent nos. 3 and 4 having 20, 40 and 100 moles of ethylene oxide per mole of nonylphenol, respectively. They are products of GAF Corporation.
6. Polyoxyethyleneglycol (PEG) (20)sorbitan monolaurate (Atlas Chemical).
7. PEG (20) sorbitol monopalmitate (Atlas Chemical).
8. PEG (20) sorbitol mono-oleate (Atlas Chemical).

Absorbance is the measure of the absorption of light. The figures provided in Table I are absorbance units based upon the ratio of transmitted to incident light. Higher absorbance signifies less light transmitted.

Signal enhancement was highest for Triton X-100, Igepal CO-630 and CO-720. The low coefficients of variations (C.V.) for Igepal CO-630 to CO-990 indicate a more rapid lysis rate compared to the other agents, including Triton X-100.

EXAMPLE II

The data provided in Table II were obtained by following the well-known procedure discussed above for fluorescent immunoassay of theophylline. In other words, the dye-containing liposomes were bound to the walls of a tube prior to introduction of the lysing agent, 2% Igepal CO-720. The fluorescence signals (relative fluorescence units. RFU) generated by the fluorometer immediately after addition of lysing agent, two minutes later, and two hours later are shown for three different concentrations of theopylline.

| Theophylline μg/ml | RFU Immediate | RFU 2 min. | % Change | RFU 2 hrs. | % Change |
|---|---|---|---|---|---|
| 5 | 558 | 562 | 0.72 | 573 | 2.7 |
|   | 558 | 548 | 1.3 | 555 | 0.5 |
| 10 | 489 | 485 | 0.82 | 487 | 0.41 |
|   | 491 | 483 | 1.6 | 487 | 0.82 |
| 30 | 339 | 343 | 1.2 | 344 | 1.5 |
|   | 317 | 314 | 0.952 | 315 | 0.63 |
|   |   | x | 1.10% | x = | 1.01% |

The above data demonstrates the stability of the signals obtained through the use of Igepal CO-720, and therefore the rapid lysis of the relatively hard theophylline liposomes.

EXAMPLE III

The FIA procedure described above was again used to obtain the data shown in Table III. Digoxin liposomes bound to a test tube in accordance with standard FIA procedure were lysed with two percent concentrations of Igepal CO-720. This is the preferred concentration of both compounds used in accordance with the invention. The table shows the signals generated by the fluorometer (RFU) for ten samples at ambient temperature wherein lysing was commenced at various intervals subsequent to washing the incubated test tubes with a saline solution.

| Wash Interval Min. | LYSIS TIME RFU | | | |
|---|---|---|---|---|
|   | 0 | 1 hr. | 2 hrs. | 16 hrs. |
| 0 | 417 | 420 | 426 | 448 |
| 5 | 395 | 404 | 403 | 425 |
| 10 | 409 | 420 | 412 | 446 |
| 15 | 380 | 384 | 387 | 413 |
| 20 | 330 | 344 | 352 | 380 |
| 25 | 349 | 377 | 379 | 419 |
| 30 | 350 | 363 | 366 | 411 |
| 35 | 318 | 338 | 312 | 385 |
| 40 | 331 | 348 | 350 | 392 |
| 45 | 333 | 349 | 358 | 403 |
| x | 361 | 375 | 375 | 412 |
| % C.V. | 10.0 | 8.4 | 9.1 | 5.7 |

The above data demonstrate the importance of adding the Igepal CO-720 to the bound liposomes as soon as possible after the washing step.

Of the two compounds employed in accordance with the method of the invention, the use of

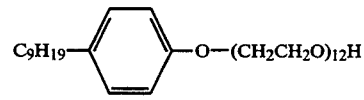

is preferred when the five factors discussed above are taken into consideration

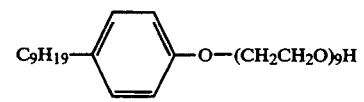

appears to be a slightly better lysing agent, however.

Although illustrative embodiments of the present invention have been described herein, it is to be understood that the invention is not limited to those precise embodiments, and that various other changes and modifications may be effected therein by one skilled in the art without departing from the scope or spirit of the invention.

What is claimed is:

1. A method for lysing liposomes comprising saturated fatty acid phosphatides and having transition temperatures in the range of 35° C. to 65° C. comprising treating the liposomes to be lysed with a surfactant selected from

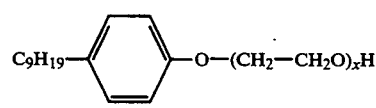

wherein the average value of x is 9 or 12.

2. A method according to claim 1 wherein the average value of x is 9.

3. A method according to claim 1 wherein the average value of x is 12.

4. A method according to claim 1 wherein said liposomes contain $C_{18}:0$ fatty acid phosphatides as one of the membrane constituents of said liposomes.

5. A method according to claim 1 wherein said liposomes contain $C_{18}:0$ distearoyl phosphatides as one of the membrane constituents of said liposomes.

6. A method according to claim 1 including the step of binding said liposomes to a surface prior to treating said liposomes with said surfactant.

7. A method according to claim 6 wherein said liposomes contain a fluorescent dye.

8. A method according to claim 1 wherein said liposomes contain a fluorescent dye, including the step of measuring the fluorescence released from said liposomes subsequent to treating said liposomes with said surfactant.

9. A method according to claim 2 wherein said liposomes contain a fluorescent dye, including the step of measuring the fluorescence released from said liposomes subsequent to treating said liposomes with said surfactant.

10. A method according to claim 3 wherein said liposomes contain a fluorescent dye, including the step of measuring the fluorescence released from said liposomes subsequent to treating said liposomes with said surfactant.

11. A method according to claim 1 wherein said liposomes are digoxin liposomes.

* * * * *

UNITED STATES PATENT AND TRADEMARK OFFICE
CERTIFICATE OF CORRECTION

PATENT NO. : 5,366,895
DATED : November 22, 1994
INVENTOR(S) : L. Pollack, et al It is certified that error appears in the above-indentified patent and that said Letters Patent is hereby corrected as shown below:

Column 1, line 22 - replace the word [razes] with --rates--
Column 1, line 27 - replace the word [L-aphosphatidylcholine] with
    --L-a-phosphatidylcholine--
Column 1, line 32 - replace the word [p-toctylphenol] with --p-t-octylphenol--

Signed and Sealed this

Second Day of May, 1995

*Attest:*

BRUCE LEHMAN

*Attesting Officer*    Commissioner of Patents and Trademarks

UNITED STATES PATENT AND TRADEMARK OFFICE
CERTIFICATE OF CORRECTION

PATENT NO. : 5,366,895
DATED : November 22, 1994
INVENTOR(S) : L. Pollack, et al It is certified that error appears in the above-indentified patent and that said Letters Patent is hereby corrected as shown below:

Column 3, line 23, add the word —signal— after the word "unquenched".

Column 4, line 56, replace the word "fluorometrically" with —photometrically—.

Signed and Sealed this

Twentieth Day of June, 1995

*Attest:*

BRUCE LEHMAN

*Attesting Officer*          *Commissioner of Patents and Trademarks*